US009974440B2

(12) United States Patent
Tsujita

(10) Patent No.: US 9,974,440 B2
(45) Date of Patent: May 22, 2018

(54) PHOTOACOUSTIC IMAGE GENERATION DEVICE AND METHOD

(71) Applicant: FUJIFILM Corporation, Tokyo (JP)

(72) Inventor: Kazuhiro Tsujita, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 767 days.

(21) Appl. No.: 14/469,626

(22) Filed: Aug. 27, 2014

(65) Prior Publication Data
US 2014/0371571 A1 Dec. 18, 2014

Related U.S. Application Data

(63) Continuation of application No. PCT/JP2013/000929, filed on Feb. 20, 2013.

(30) Foreign Application Priority Data

Feb. 28, 2012 (JP) ................. 2012-040977

(51) Int. Cl.
*A61B 8/00* (2006.01)
*A61B 5/00* (2006.01)
*A61B 8/08* (2006.01)

(52) U.S. Cl.
CPC .......... *A61B 5/0095* (2013.01); *A61B 5/7257* (2013.01); *A61B 5/742* (2013.01);
(Continued)

(58) Field of Classification Search
CPC ....... A61B 5/0095; A61B 5/7257; A61B 8/13; A61B 8/5269
See application file for complete search history.

(56) References Cited

U.S. PATENT DOCUMENTS 5,136,172 A * 8/1992 Nakata ............... G01N 21/1702
250/559.39
2005/0187471 A1 8/2005 Kanayama et al.
(Continued)

FOREIGN PATENT DOCUMENTS

JP 7-282247 A 10/1995
JP 2005-218684 A 8/2005
JP 2011-217767 A 11/2011

OTHER PUBLICATIONS

Calasso et al., "Photoacoustic Point Source", Physical Review Letters, vol. 86, No. 16, Apr. 16, 2001, pp. 3550-3553.
(Continued)

*Primary Examiner* — Joel Lamprecht
(74) *Attorney, Agent, or Firm* — Birch, Stewart, Kolasch & Birch, LLP

(57) ABSTRACT

A desired structure is selectively imaged by photoacoustic imaging. Photoacoustic signals are detected, and the detected photoacoustic signals are reconstructed to generate photoacoustic image data. A Fourier transform in a two-dimensional or higher dimensional space is applied to the photoacoustic image data to generate spatial frequency domain photoacoustic image data. Given spatial frequency components are extracted from the spatial frequency domain photoacoustic image data, and an inverse Fourier transform is applied to the extracted spatial frequency components to generate spatial frequency-processed photoacoustic image data.

20 Claims, 10 Drawing Sheets

(52) U.S. Cl.
CPC .......... *A61B 8/0891* (2013.01); *A61B 8/5207* (2013.01); *A61B 8/5215* (2013.01); *A61B 8/54* (2013.01); *A61B 2576/00* (2013.01)

(56) References Cited

U.S. PATENT DOCUMENTS

| | | | | |
|---|---|---|---|---|
| 2005/0234319 | A1* | 10/2005 | Mandelis | G01B 21/085 600/407 |
| 2007/0179365 | A1* | 8/2007 | Bitton | A61B 5/0059 600/310 |
| 2011/0060211 | A1* | 3/2011 | Lorenzo | A61B 5/0071 600/411 |
| 2011/0066023 | A1 | 3/2011 | Kanayama et al. | |
| 2011/0282181 | A1* | 11/2011 | Wang | A61B 5/0095 600/407 |
| 2012/0029829 | A1* | 2/2012 | Li | A61B 5/0059 702/19 |
| 2012/0179041 | A1* | 7/2012 | Nakagawa | A61B 5/0073 600/443 |
| 2012/0296192 | A1* | 11/2012 | Fukutani | A61B 5/0095 600/407 |
| 2013/0039147 | A1* | 2/2013 | Witte | A61B 5/0093 367/7 |
| 2013/0137959 | A1* | 5/2013 | Lisogurski | A61B 5/0095 600/407 |
| 2013/0184544 | A1* | 7/2013 | Su | A61B 5/0095 600/323 |
| 2013/0245420 | A1* | 9/2013 | Fukutani | A61B 5/72 600/407 |

OTHER PUBLICATIONS

International Search Report, issued in PCT/JP2013/000929, dated May 7, 2013.
Written Opinion of the International Searching Authority, issued in PCT/JP2013/000929, dated May 7, 2013.

* cited by examiner

WAVE NUMBER SPACE

WAVE NUMBER SPACE

WAVE NUMBER SPACE

PHOTOACOUSTIC IMAGE GENERATION DEVICE AND METHOD

CROSS-REFERENCE TO RELATED APPLICATIONS

This application is a Continuation of PCT International Application No. PCT/JP2013/000929 filed on Feb. 20, 2013, which claims priority under 35 U.S.C. § 119(a) to Japanese Patent Application No. 2012-040977 filed on Feb. 28, 2012. Each of the above application(s) is hereby expressly incorporated by reference, in its entirety, into the present application.

BACKGROUND OF THE INVENTION

Technical Field

The present invention relates to a photoacoustic image generation device and a photoacoustic image generation method, and more particularly to a photoacoustic image generation device and a photoacoustic image generation method that involves applying light to a subject, and generating a photoacoustic image by detecting acoustic waves that are emitted from the interior of the subject due to the applied light.

Background Art

Ultrasonography is known as one of imaging examination methods that allow non-invasive examination of state of the interior of a living body. In ultrasonography, an ultrasound probe that can transmit and receive ultrasound is used. Ultrasound transmitted from the ultrasound probe to the subject (living body) travels through the interior of the living body and is reflected at a tissue interface. Then, the reflected ultrasound is received by the ultrasound probe. Based on the time taken for the reflected ultrasound to return to the ultrasound probe, the distance is calculated, thereby imaging the state of the interior.

Further, photoacoustic imaging, which images the interior of a living body using the photoacoustic effect, is known. In photoacoustic imaging, in general, pulsed laser light is applied to the interior of a living body. In the interior of the living body, a living tissue absorbs energy of the pulsed laser light, and ultrasound (photoacoustic signals) is emitted due to adiabatic expansion caused by the energy. The photoacoustic signals are detected using an ultrasound probe, or the like, and a photoacoustic image is constructed based on the detected signals, thereby visualizing the interior of the living body based on the photoacoustic signals.

With respect to the photoacoustic imaging, Japanese Unexamined Patent Publication No. 2011-217767 (hereinafter, Patent Document 1) teaches that spatial frequency processing is performed. With the technique of Patent Document 1, light from a light source is applied to a subject, and photoacoustic signals are detected with a plurality of detector elements. The detected photoacoustic signals include photoacoustic signals emitted from the surface of the subject and photoacoustic signals emitted from the interior of the subject. With the technique of Patent Document 1, signals detected by the detector elements at the same reception time are subjected to a Fourier transform in the spatial direction to obtain spatial frequency signals. Then, components of frequencies not greater than a predetermined frequency of the spatial frequency signals are reduced. Then, the spatial frequency signals with reduced low-frequency components are subjected to an inverse Fourier transform, and a photoacoustic image is generated based on the signals obtained by the inverse transform. The photoacoustic signals emitted from the surface of the subject are simultaneously obtained with the plurality of detector elements, and therefore imaging with reduced influence of the photoacoustic waves emitted from the surface of the subject can be achieved.

With respect to the spatial frequency processing, Japanese Unexamined Patent Publication No. 7(1995)-282247 (hereinafter, Patent Document 2) teaches that image data obtained by ultrasound imaging is subjected to a Fourier transform to generate spatial frequency domain image data, and predetermined low-frequency components are removed from the Fourier-transformed spatial frequency domain image data. Then, the spatial frequency domain image data from which the low-frequency components have been removed is subjected to an inverse transform to generate image data of real data domain. Patent Document 2 teaches that the low-frequency components are equivalent to shading, and image portions that are necessary for diagnosis are not present in the low-frequency range, and therefore removing the components of low spatial frequencies is equivalent to removing shading. That is, in Patent Document 2, a desired area to be observed in the image data is present in the high-frequency range in the spatial frequency domain. Therefore, the low-frequency range in the spatial frequency domain is removed to remove areas other than the necessary area.

DISCLOSURE OF THE INVENTION

A part to be imaged by the photoacoustic imaging may, for example, be blood vessels. There are blood vessels of various sizes, such as thick blood vessels and thin blood vessels, and enabling imaging of blood vessels of a desired size is believed to be useful for diagnostic imaging. With the technique of Patent Document 1, however, the detection signals of photoacoustic waves which are detected at the same time are subjected to the Fourier transform in the spatial direction, and therefore extraction and imaging of blood vessels of a desired size cannot be achieved. With the technique of Patent Document 2, what is processed is an ultrasound image, and the spatial frequency processing for removing low-frequency components is performed simply because that the desired area to be observed is present in the high-frequency range of the spatial frequency domain, and therefore extraction and imaging of a desired structure cannot be achieved.

In view of the above-described circumstances, the present invention is directed to providing a photoacoustic image generation device and a photoacoustic image generation method that allow selectively imaging and emphasizing a desired structure by photoacoustic imaging.

In order to accomplish the above-described object, the invention provides a photoacoustic image generation device comprising: a light source that emits light to be applied to a subject; an acoustic wave detection means that detects photoacoustic waves emitted from the interior of the subject due to the light applied to the subject; a photoacoustic image generation means that reconstructs photoacoustic signals to generate image data, the photoacoustic signals being detection signals of the photoacoustic waves; a Fourier transform means that applies a Fourier transform in a two-dimensional or higher dimensional space to the image data to generate spatial frequency domain image data; a spatial frequency processing means that extracts given spatial frequency components from the spatial frequency domain image data; and an inverse Fourier transform means that applies an inverse Fourier transform to the extracted spatial frequency components to generate spatial frequency-processed image data.

The spatial frequency processing means may extract spatial frequency components of frequencies not lower than a first spatial frequency and not higher than a second spatial frequency that is higher than the first spatial frequency.

The first spatial frequency and the second spatial frequency may be changed depending on a position in the spatial frequency domain (wave number space).

In the invention, the spatial frequency processing means may determine the given spatial frequency components to be extracted according to an observation object condition specified by the user.

A cross-sectional image generation means that cuts out, from three-dimensional image data based on three-dimensionally detected photoacoustic waves, a cross-section along a plane perpendicular to one of axes forming a three-dimensional space, and generates cross-sectional image data by combining image data within a predetermined range in a direction along the one axis including the cut-out cross-section may further be provided, wherein the Fourier transform means may apply a two-dimensional Fourier transform to the cross-sectional image data.

The cross-sectional image generation means may cut out cross-sections at a plurality of positions along the one axis to generate pieces of cross-sectional image data, the Fourier transform means may apply a Fourier transform to each of the generated pieces of cross-sectional image data to generate pieces of spatial frequency domain image data, the spatial frequency processing means may extract given spatial frequency components from each of the generated pieces of spatial frequency domain image data, and the inverse Fourier transform means may apply an inverse Fourier transform to the given spatial frequency components extracted from each of the pieces of spatial frequency domain image data to generate spatial frequency-processed cross-sectional image data for each of the pieces of cross-sectional image data.

The cross-sectional image generation means may cut out the cross-sections at equal intervals.

The cross-sectional image generation means may cut out the cross-section in a direction parallel to an acoustic wave detection surface of the acoustic wave detection means while changing the position of the cut-out cross-section along an axis corresponding to a depth direction of the subject.

The cross-sectional image generation means may combine the image data within the predetermined range by projecting maximum values of the image data within the predetermined range or integrating the image data within the predetermined range.

An image display control means that displays, on a display device, spatial frequency-processed cross-sectional image data obtained by applying an inverse Fourier transform to given spatial frequency components extracted from the spatial frequency domain cross-sectional image data may further be provided.

A cross-section position selection means that determines a cross-section position of cross-sectional image data to be displayed according to a user's operation may further be provided, wherein the display control means may display, on the display device, the spatial frequency-processed cross-sectional image data corresponding to a cross-section position specified by the user.

The display control means may display, on the display device, a slide bar used to specify the cross-section position, and the cross-section position selection means may determine the cross-section position according to operation of the slide bar by the user.

The display control means may display cross-sectional image data that has not been subjected to spatial frequency processing and the spatial frequency-processed cross-sectional image data side by side on the display device.

The display control means may binarize the spatial frequency-processed cross-sectional image data and may display the binarized spatial frequency-processed cross-sectional image data on the display device.

The Fourier transform means may apply a three-dimensional Fourier transform to three-dimensional image data based on three-dimensionally detected photoacoustic waves.

The light source may emit a plurality of different wavelengths of light, the acoustic wave detection means may detect photoacoustic waves emitted from the interior of the subject after each of the plurality of wavelengths of light is applied to the subject, the photoacoustic image generation means may reconstruct the detected photoacoustic signals corresponding to each of the plurality of wavelengths of light to generate image data, the Fourier transform means may apply a Fourier transform to the image data corresponding to each of the plurality of wavelengths of light, the spatial frequency processing means may extract given spatial frequency components corresponding to each of the plurality of wavelengths of light from the Fourier-transformed spatial frequency domain image data corresponding to each wavelength, and the inverse Fourier transform means may apply an inverse Fourier transform to each of the extracted spatial frequency components.

The plurality of wavelengths of light may comprise light of a first wavelength and light of a second wavelength, and the spatial frequency components extracted by the spatial frequency processing means from the spatial frequency domain image data corresponding to the light of the first wavelength and the spatial frequency components extracted by the spatial frequency processing means from the spatial frequency domain image data corresponding to the light of the second wavelength may be different from each other.

A deconvolution means that deconvolves, from the photoacoustic signals, a differential waveform of the light applied to the subject may further be provided.

The invention also provides a photoacoustic image generation method comprising the steps of: applying light from a light source to a subject; detecting photoacoustic waves emitted from the interior of the subject due to the light applied to the subject; reconstructing photoacoustic signals to generate image data, the photoacoustic signals being detection signals of the photoacoustic waves; applying a Fourier transform in a two-dimensional or higher dimensional space to the image data to generate spatial frequency domain image data; extracting given spatial frequency components from the spatial frequency domain image data; and applying an inverse Fourier transform to the extracted spatial frequency components to generate spatial frequency-processed image data.

The photoacoustic image generation device and method of the invention apply a Fourier transform to image data, which is obtained by reconstructing photoacoustic signals, to convert the image data into spatial frequency domain image data, and extracts given spatial frequency components from the spatial frequency domain image data. An inverse Fourier transform is applied to the extracted spatial frequency components to generate spatial frequency-processed image data. By appropriately selecting the spatial frequency components to be extracted depending on the size, etc., of an object to be observed, a desired structure can be selectively imaged.

DESCRIPTION OF PREFERRED EMBODIMENTS

Figure 1:
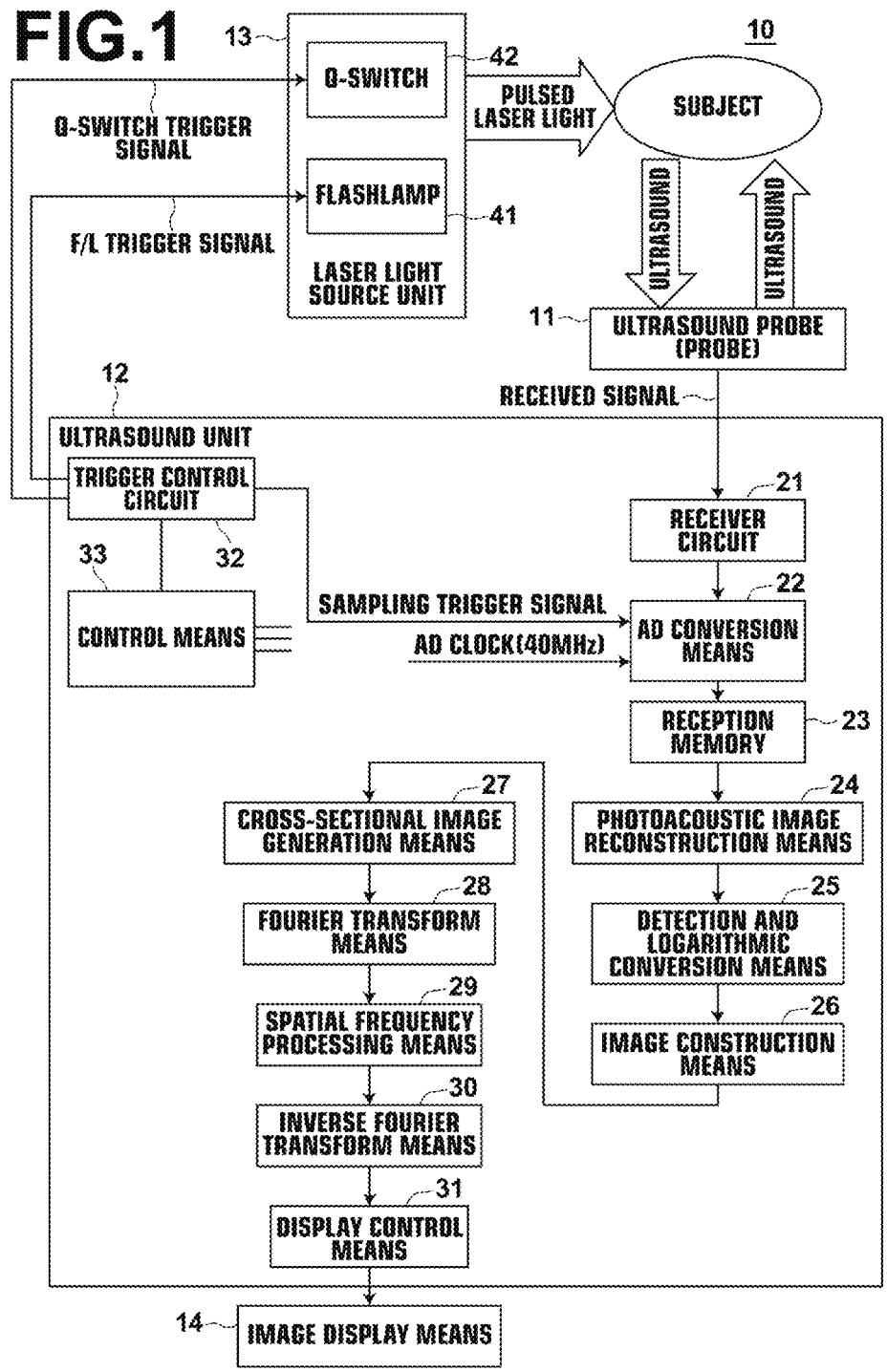
FIG. 1 is a block diagram illustrating a photoacoustic image generation device according to a first embodiment of the invention.

Hereinafter, embodiments of the present invention will be described in detail with reference to the drawings. FIG. 1 shows a photoacoustic image generation device according to a first embodiment of the invention. A photoacoustic image generation device (photoacoustic diagnostic imaging device) 10 includes an ultrasound probe (probe) 11, an ultrasound unit 12, and a light source (laser unit) 13.

The laser unit 13 is a light source and generates light (laser light) to be applied to a subject. The wavelength of the laser light may be set as appropriate depending on the object to be observed. The laser unit 13 emits light having a wavelength (specifically, 750 nm or 800 nm) that is highly absorbed by hemoglobin, for example. The laser light emitted from the laser unit 13 is guided to the probe 11 via a light guide means, such as optical fibers, and is applied to the subject from the probe 11. Alternatively, the light may be applied to the subject from a position other than the probe 11.

The probe 11 includes an acoustic wave detection means that detects acoustic waves (ultrasound) emitted from the interior of the subject. The acoustic wave detection means includes a plurality of ultrasound transducers, which are one-dimensionally arranged, for example. The probe 11 detects, with the ultrasound transducers, photoacoustic waves (which may hereinafter also be referred to as "photoacoustic signals") emitted from an object to be measured in the subject which has absorbed the light from the laser unit 13.

The ultrasound unit 12 includes a receiver circuit 21, an AD conversion means 22, a reception memory 23, a photoacoustic image reconstruction means 24, a detection and logarithmic conversion means 25, an image construction means 26, a cross-sectional image generation means 27, a Fourier transform means 28, a spatial frequency processing means 29, an inverse Fourier transform means 30, a display control means 31, a trigger control circuit 32, and a control means 33. The control means 33 controls the individual components of the ultrasound unit 12. The receiver circuit 21 receives detection signals (photoacoustic signals) of the photoacoustic waves detected by the probe 11. The AD conversion means 22 samples the photoacoustic signals received by the receiver circuit 21 and converts the photoacoustic signals into digital signals. The AD conversion means 22 samples the photoacoustic signals at a predetermined sampling cycle synchronously with an AD clock signal, for example.

The trigger control circuit 32 outputs a light trigger signal, which instructs to emit light, to the laser unit 13. The laser unit 13 includes a flashlamp 41 that excites a laser medium (not shown), such as YAG or titanium-sapphire, and a Q-switch 42 that controls laser oscillation. When the trigger control circuit 32 outputs a flashlamp trigger signal, the laser unit 13 turns on the flashlamp 41 to excite the laser medium. When the laser medium is sufficiently excited by the flashlamp 41, for example, the trigger control circuit 32 outputs a Q-switch trigger signal. In response to the Q-switch trigger signal, the Q-switch 42 is turned on, and laser light is emitted from the laser unit 13. The time taken for the laser medium to be sufficiently excited after the flashlamp 41 is turned on can be estimated from characteristics, etc., of the laser medium.

It should be noted that, in place of controlling the Q-switch by the trigger control circuit 32, the Q-switch 42 may be turned on by the laser unit 13 after the laser medium is sufficiently excited. In this case, a signal indicating that the Q-switch 42 has been turned on may be sent to the ultrasound unit 12. It should be noted that the light trigger signal is a concept that includes at least one of the flashlamp trigger signal and the Q-switch trigger signal. In the case where the Q-switch trigger signal is outputted from the trigger control circuit 32, the Q-switch trigger signal corresponds to the light trigger signal. On the other hand, in the case where timing of the Q-switch trigger is generated in the laser unit 13, the flashlamp trigger signal may correspond to the light trigger signal. When the light trigger signal is outputted, the laser light is applied to the subject, and the photoacoustic signals are detected.

Further, the trigger control circuit 32 outputs a sampling trigger signal, which instructs to start sampling, to the AD conversion means 22. The trigger control circuit 32 outputs the sampling trigger signal at predetermined timing after output of the light trigger signal. It is preferable that the trigger control circuit 32 output the sampling trigger signal at timing when the laser light is actually applied to the subject after output of the light trigger signal. For example, the trigger control circuit 32 outputs the sampling trigger signal synchronously with output of the Q-switch trigger signal. In response to the sampling trigger signal, the AD conversion means 22 starts sampling of the photoacoustic signals detected by the probe 11.

The AD conversion means 22 stores the sampled photoacoustic signals in the reception memory 23. As the reception memory 23, a semiconductor storage device may be used, for example. Alternatively, other types of storage devices, such as a magnetic storage device, may be used as the reception memory 23. In the reception memory 23, sampled data (photoacoustic data) of the photoacoustic signals is stored.

The photoacoustic image reconstruction means 24 reads out the photoacoustic signals from the reception memory 23 and reconstructs the read-out photoacoustic signals. The photoacoustic image reconstruction means 24 generates image data of each line of a photoacoustic image, which is a tomographic image, based on the photoacoustic signals. The reconstructed photoacoustic signals can be regarded as a photoacoustic image. The photoacoustic image reconstruction means 24 reconstructs the photoacoustic signals using a delay-and-sum method (which is synonymous with phase matching addition or phasing addition). The photoacoustic image reconstruction means 24 generates data of each one line by summing photoacoustic signals corresponding to 64 elements, for example, with a delay time depending on the position of each element (each ultrasound transducer). At this time, the speed of sound in the subject may be assumed to be constant, or the delay time for each element may be corrected with taking a sound speed distribution into account. In place of the delay-and-sum method, a Hough transform method or a Fourier transform method may be used to perform the reconstruction.

The detection and logarithmic conversion means 25 generates an envelope to the data of each line outputted from the photoacoustic image reconstruction means 24, and applies logarithmic conversion to the envelope to increase the dynamic range. The image construction means 26 generates a photoacoustic image based on the data of each line having been subjected to the logarithmic conversion. For example, the image construction means 26 generates the photoacoustic image by converting positions in the time axis direction of the photoacoustic signals (peak portions) into positions in the depth direction of the tomographic image. The photoacoustic image reconstruction means 24, the detection and logarithmic conversion means 25, and the image construction means 26 correspond to a photoacoustic image generation means. For example, the photoacoustic image generation means generates three-dimensional image data based on three-dimensionally detected photoacoustic waves.

The cross-sectional image generation means 27 cuts out a cross-section of a given plane from the three-dimensional photoacoustic image data. For example, the cross-sectional image generation means 27 cuts out image data along a plane perpendicular to one of axes forming the three-dimensional space. The cross-sectional image generation means 27 generates cross-sectional image data by combining pieces of image data within a predetermined range including the cut-out cross-section in a direction perpendicular to the cross-section. For example, in a case where the cross-sectional image generation means 27 cuts outs a cross-section along a plane parallel to the acoustic wave detection surface of the probe 11 at a position along an axis corresponding to the depth direction of the subject, the cross-sectional image generation means 27 combines predetermined number of cross-sectional images in the shallower direction and the deeper direction from the position of the cut-out cross-section into one image. The cross-sectional image generation means 27 combines pieces of image data within the predetermined range into one image data by, for example, projecting maximum values of the pieces of image data within the predetermined range. Alternatively, the cross-sectional image generation means 27 may combine pieces of image data within the predetermined range by integrating (averaging) the pieces of image data.

The Fourier transform means 28 applies a Fourier transform to the photoacoustic image data to generate spatial frequency domain image data. In this embodiment, the Fourier transform means 28 applies a two-dimensional Fourier transform to the cross-sectional image data generated by the cross-sectional image generation means 27. The spatial frequency processing means 29 extracts given spatial frequency components from the Fourier-transformed spatial frequency domain image data. For example, the spatial frequency processing means 29 selectively extracts spatial frequency components of frequencies not lower than a first spatial frequency and not higher than a second spatial frequency that is higher than the first spatial frequency from the spatial frequency domain image data.

The inverse Fourier transform means 30 applies an inverse Fourier transform to the spatial frequency components extracted by the spatial frequency processing means 29 to generate spatial frequency-processed image data. The display control means 31 displays the spatial frequency-processed cross-sectional image data, which results from the inverse transform by the inverse Fourier transform means 30, on the display screen of the image display means 14, such as a display device. The display control means 31 may binarize the spatial frequency-processed cross-sectional image data that is grayscale data, for example, to display the binarized image data on the display device.

Figure 2:
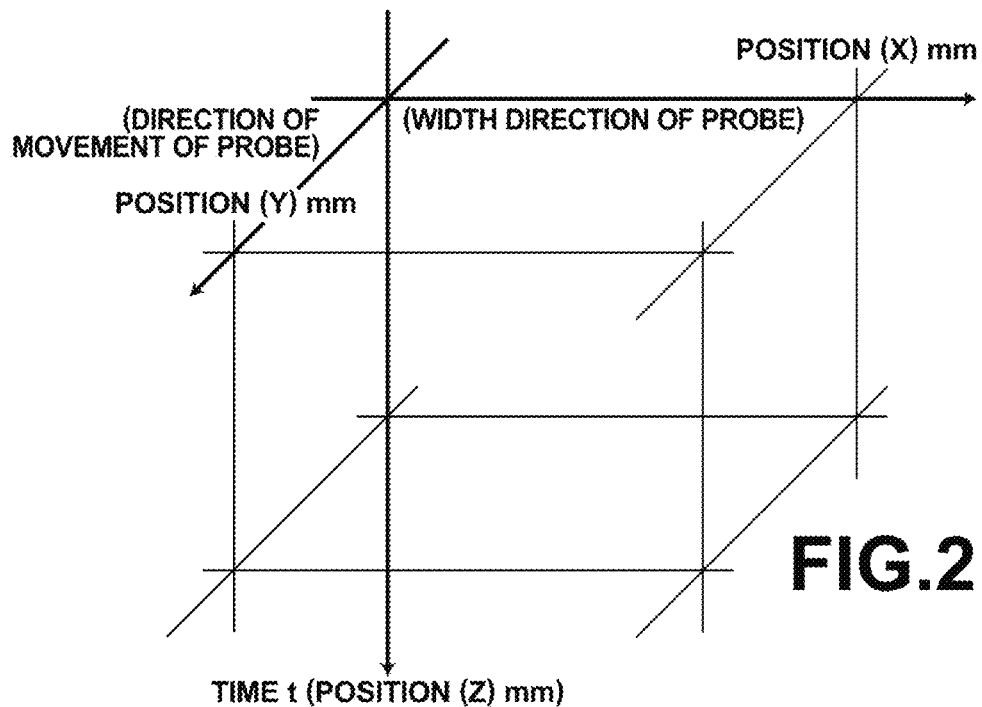
FIG. 2 is a diagram illustrating a photoacoustic signal detection space.

FIG. 2 shows a photoacoustic signal detection space. The time direction of photoacoustic signals corresponds to the depth direction (Z-direction) of a photoacoustic image. The probe 11 includes a plurality of detector elements (ultrasound transducers), which are one-dimensionally arranged in the X-direction, for example. By moving the above-described probe 11 to scan in the Y-direction, photoacoustic signals can be obtained three-dimensionally. In place of scanning with the probe including one-dimensionally arranged detector elements, a probe including a plurality of detector elements that are two-dimensionally arranged in the X-direction and the Y-direction may be used. In this case, photoacoustic signals can be three-dimensionally obtained without moving the probe for scanning.

Figure 3:
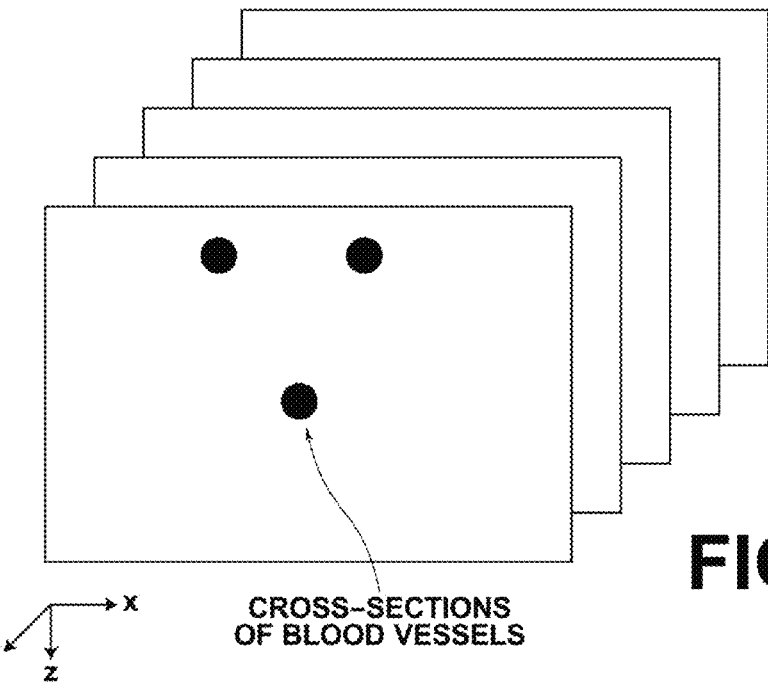
FIG. 3 is a diagram illustrating tomographic images of X-Z cross-sections.

FIG. 3 shows tomographic images (photoacoustic images) of X-Z cross-sections. For example, in the case where the probe 11 includes a plurality of ultrasound transducers arranged in the X-direction, the photoacoustic image generation means generates a photoacoustic image of an X-Z cross-section. For example, assuming that blood vessel are transverse in the Y-direction, circular cross-sections of the blood vessels appear in a photoacoustic image of an X-Z cross-section. By moving the probe 11 to scan in the Y-direction to generate a photoacoustic image of an X-Z cross-section at each scanning position and joining the thus obtained cross-sectional images, three-dimensional photoacoustic image data can be obtained.

Figure 4:
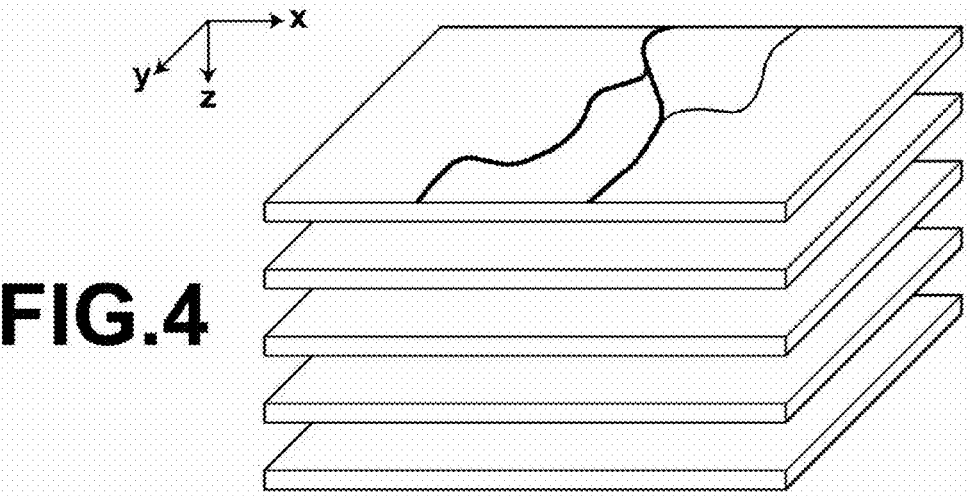
FIG. 4 is a diagram illustrating cross-sectional images generated by a cross-sectional image generation means.

FIG. 4 shows cross-sectional images generated by the cross-sectional image generation means 27. For example, the cross-sectional image generation means 27 cuts out, from the three-dimensional photoacoustic image data, cross-sections in planes (X-Y planes) parallel to the acoustic wave detection surface of the probe 11 while changing the position of the cut-out cross-section along the Z-axis, and generates cross-sectional image data by combining a predetermined number of pieces of image data. For example, the cross-sectional image generation means 27 generates one piece of cross-sectional image data by projecting maximum values of pieces of image data of the number corresponding to a thickness of 2 mm in the depth direction (Z-direction). For example, the cross-sectional image generation means 27 cuts out cross-sections at positions at equal intervals along the Z-axis and generates a piece of cross-sectional image data corresponding to every two millimeters. The cross-sectional image generated by the cross-sectional image generation means 27 is not limited to a cross-sectional image parallel to an X-Y plane. The cross-sectional image generation means 27 may generate a cross-sectional image that is parallel to an X-Z plane or a Y-Z plane.

The Fourier transform means 28 applies a Fourier transform to each of the pieces of cross-sectional image data shown in FIG. 4 to generate pieces of spatial frequency domain cross-sectional image data. The spatial frequency processing means 29 extracts given spatial frequency components from each of the thus generated pieces of spatial frequency domain cross-sectional image data. The inverse Fourier transform means 30 applies an inverse Fourier transform to the given spatial frequency components extracted from each of the pieces of spatial frequency domain cross-sectional image data. By applying the inverse transform, pieces of spatial frequency-processed cross-sectional image data are generated from the pieces of cross-sectional image data shown in FIG. 4. By joining the pieces of spatial frequency-processed cross-sectional image data, spatial frequency-processed three-dimensional photoacoustic image data can be obtained.

Figure 5:
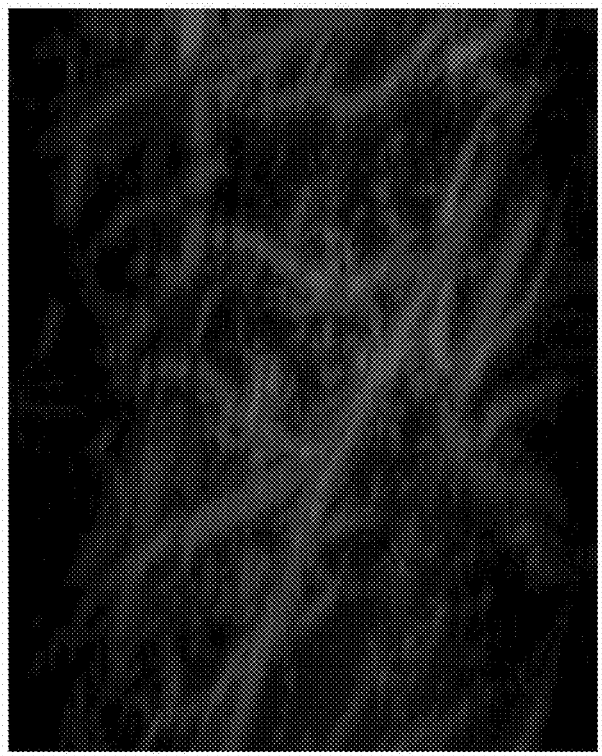
FIG. 5 shows an image example of cross-sectional image data.
Figure 6:
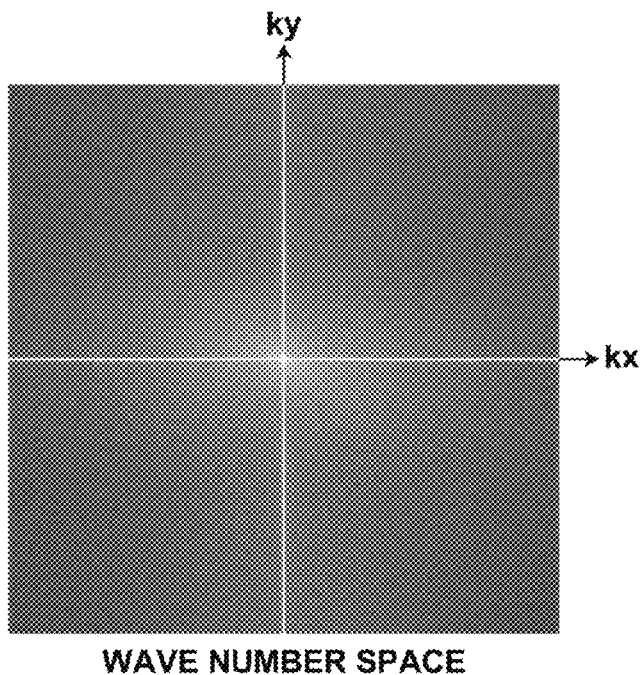
FIG. 6 shows spatial frequency domain cross-sectional image data.

FIG. 5 shows an image example of the cross-sectional image data. The image shown in FIG. 5 corresponds to one of the pieces of cross-sectional image data shown in FIG. 4. FIG. 6 shows Fourier-transformed spatial frequency domain (wave number space) cross-sectional image data. By converting the cross-sectional image data shown in FIG. 5 into spatial frequency domain data, data shown in FIG. 6 is obtained. In FIG. 6, the abscissa axis represents a wave number kx and the ordinate axis represents a wave number ky. The point of intersection between kx and ky is the origin. The nearer a spatial frequency component to the origin, the lower the frequency of the spatial frequency component.

Figure 7:
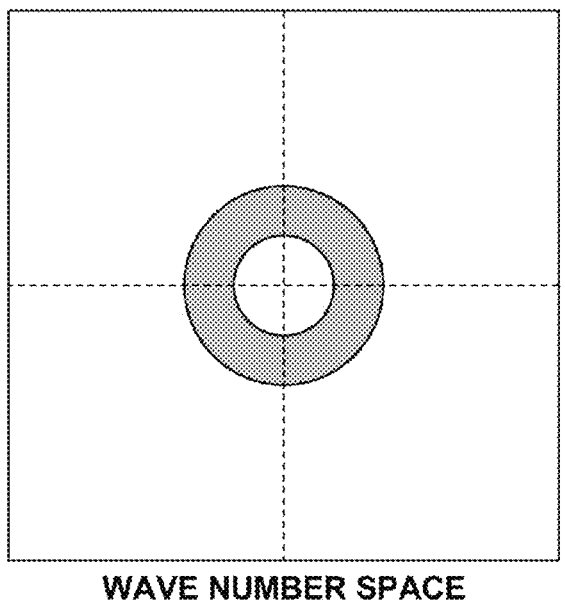
FIG. 7 is a diagram illustrating one example of a spatial frequency filter.

FIG. 7 shows one example of a spatial frequency filter applied by the spatial frequency processing means 29. In FIG. 7, the white areas represent areas cut off by the spatial frequency filter, and the gray area represents an area transmitted through the spatial frequency filter. The spatial frequency processing means 29 applies the spatial frequency filter as shown in FIG. 7, for example, to the wave number-space image data shown in FIG. 6. As a result, the spatial frequency processing means 29 removes low-frequency components within a certain distance from the origin in the wave number space and high-frequency components apart from the origin by at least another certain distance in the wave number space.

Figure 8:
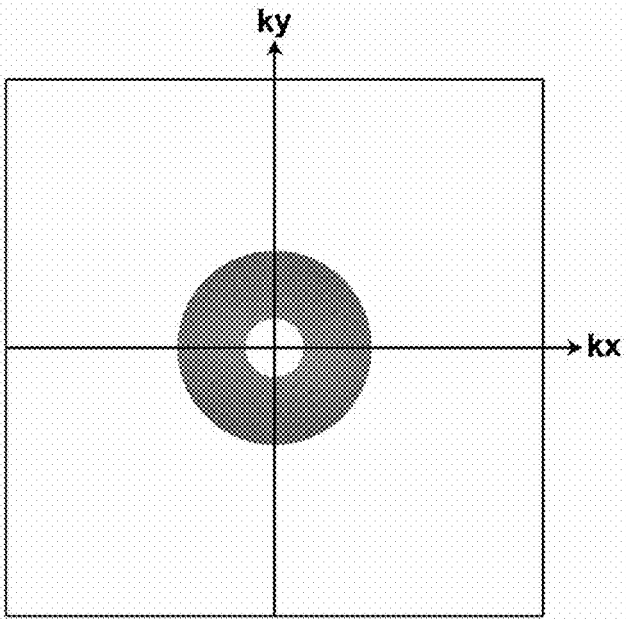
FIG. 8 shows image data of extracted given spatial frequency components.

FIG. 8 shows image data of given spatial frequency components extracted by the spatial frequency processing means 29. As shown in FIG. 8, the spatial frequency processing means 29 extracts, as data of the given spatial frequency components, data in the gray annular area shown in FIG. 7 from the spatial frequency domain image data shown in FIG. 6.

Figure 9:
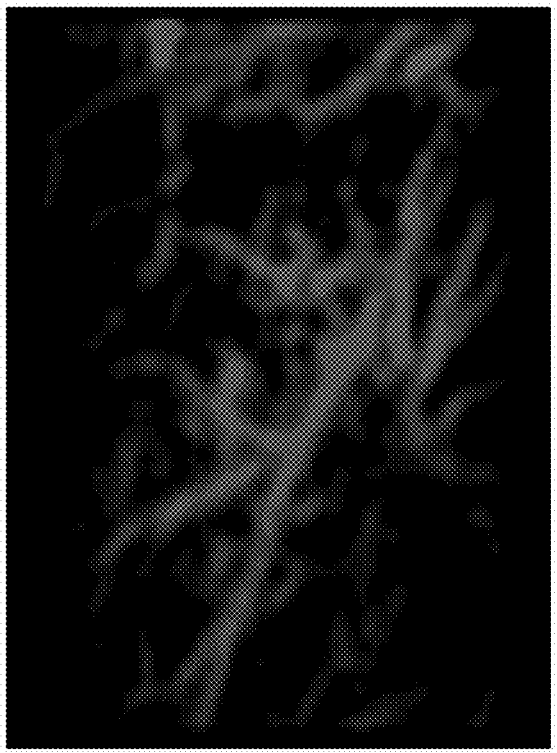
FIG. 9 shows cross-sectional image data obtained by applying an inverse Fourier transform.

FIG. 9 shows cross-sectional image data obtained by applying an inverse Fourier transform to the image data of spatial frequency components shown in FIG. 8. By selectively extracting only given spatial frequency components in the wave number space and applying an inverse Fourier transform to the extracted data, an image of portions corresponding to the given spatial frequency components can be obtained. Comparing the cross-sectional image data before the spatial frequency processing shown in FIG. 5 with the cross-sectional image data shown in FIG. 9, it can be seen that the image noise is reduced and the blood vessel portions are more visible in the cross-sectional image data shown in FIG. 9.

The spatial frequency filter shown in FIG. 7 may be determined as appropriate depending on the size, etc., of the object to be observed. For example, the user (operator) specifies, as an observation object condition, the thickness of blood vessels which the user wishes to extract. The spatial frequency processing means 29 sets a spatial frequency filter that corresponds to the specified thickness of blood vessels. As one example, when blood vessels having a thickness of 0.5 mm are specified as the object to be extracted, the spatial frequency processing means 29 sets a spatial frequency filter that selectively transmits only the frequency band (annular) that corresponds to 1 to 2 cycles/mm on the image. Alternatively, a spatial frequency filter that selectively transmits a predetermined range (for example ±α) with 2 cycles/mm being the center of the range may be set. If the thickness of blood vessels to be extracted is 1 mm, a spatial frequency filter that selectively transmits frequency components in the range from 0.3 to 0.8 cycle/mm may be used.

Although the user specifies the thickness of blood vessels which the user wishes to extract in the above-described example, the user may specify the part to be observed, in place of specifying the thickness of blood vessels. The spatial frequency processing means 29 stores in advance information of spatial frequency filters corresponding to different parts to be observed. When the user specifies the part to be observed, the spatial frequency processing means 29 reads out information of the spatial frequency filter that corresponds to the part to be observed, and sets the spatial frequency filter according to the read-out information of the spatial frequency filter.

Figure 10:
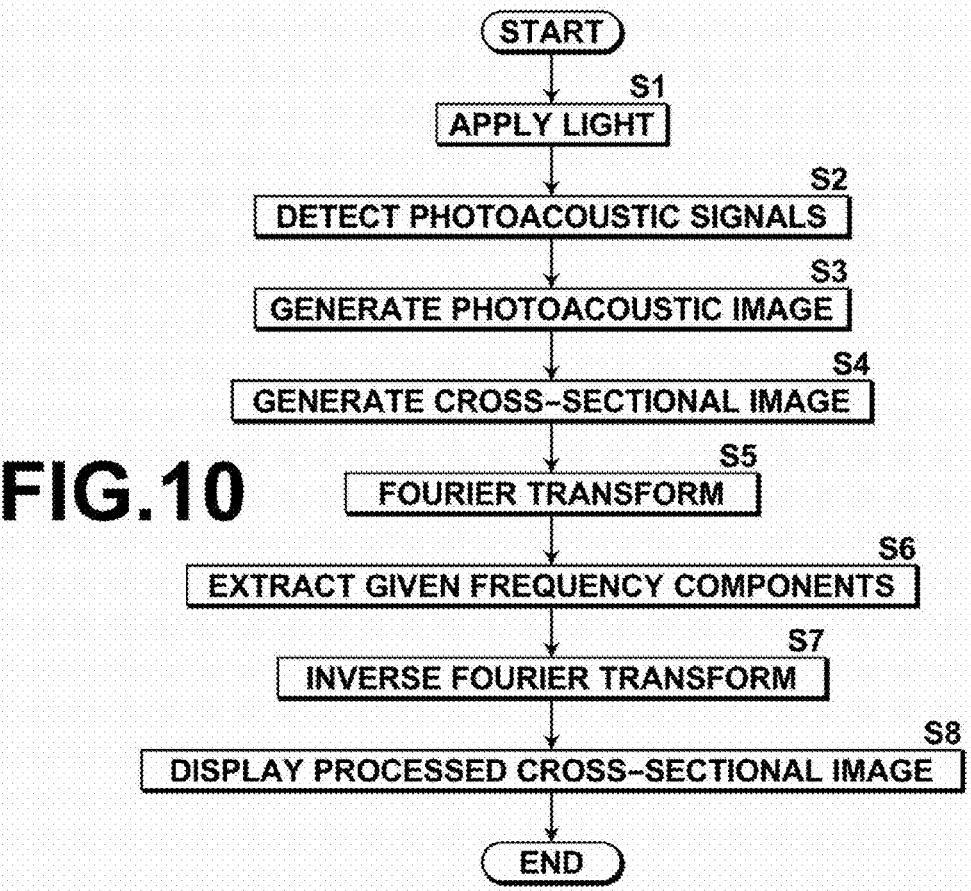
FIG. 10 is a flow chart illustrating an operation procedure of the photoacoustic image generation device.

Next, the operation procedure is described. FIG. 10 shows the operation procedure of the photoacoustic image generation device 10. The trigger control circuit 32 outputs a flashlamp trigger signal to the laser unit 13. At the laser unit 13, the flashlamp 41 is turned on in response to the flashlamp trigger signal to start excitation of the laser medium. The trigger control circuit 32 sends a Q-switch trigger signal to the laser unit 13 to turn on the Q-switch 42, thereby causing the laser unit 13 to emit pulsed laser light (step S1). For example, the trigger control circuit 32 outputs the Q-switch trigger signal at timing that has a predetermined temporal relationship with timing at which the flashlamp trigger signal is outputted. For example, the trigger control circuit 32 outputs the Q-switch trigger signal 150 µs after emission of light from the flashlamp.

The laser light emitted from the laser unit 13 is applied to the subject. In the interior of the subject, photoacoustic signals are emitted due to the applied pulsed laser light. The probe 11 detects the photoacoustic signals emitted from the interior of the subject (step S2). The photoacoustic signals detected by the probe are inputted to the AD conversion means 22 via the receiver circuit 21. The AD conversion means 22 samples the photoacoustic signals and converts them into digital data, and stores the digital data of the photoacoustic signals in the reception memory 23. For example, three-dimensional data of photoacoustic signals can be obtained by applying light and detecting photoacoustic signals at a plurality of scanning positions while moving the probe 11 that includes one-dimensionally arranged ultrasound transducers for scanning.

The photoacoustic image reconstruction means 24 reads out the photoacoustic signals from the reception memory 23, and reconstructs the read-out photoacoustic signals. The detection and logarithmic conversion means 25 performs detection and logarithmic conversion on the reconstructed photoacoustic signals. The image construction means 26 generates a photoacoustic image based on the photoacoustic signals having been subjected to the detection and logarithmic conversion (step S3). The photoacoustic image reconstruction means 24, the detection and logarithmic conversion means 25, and the image construction means 26 generate three-dimensional photoacoustic image data from the three-dimensional data of the photoacoustic signals.

The cross-sectional image generation means 27 generates cross-sectional image data from the three-dimensional photoacoustic image data by combining a predetermined number of cross-sections in given planes (step S4). For example, the cross-sectional image generation means 27 generates each cross-sectional image data by combining cross-sections that are parallel to the acoustic wave detection surface of the probe 11, where the number of cross-sections corresponds to a predetermined thickness. By combining a plurality of images into one cross-sectional image data, even blood vessels whose positions vary in a direction perpendicular to the acoustic wave detection surface, for example, can be contained in one piece of cross-sectional image data. The Fourier transform means 28 applies a Fourier transform to each cross-sectional image generated in step S4 (step S5). The spatial frequency processing means 29 extracts given frequency components from the Fourier-transformed spatial frequency domain cross-sectional image data (step S6). The inverse Fourier transform means 30 applies an inverse Fourier transform to the data of the extracted given frequency components (step S7).

The display control means 31 displays the cross-sectional image data resulting from the inverse-transform on the display screen of the image display means 14 (step S8). The display control means 31 may display pieces of spatial frequency-processed cross-sectional image data, which correspond to pieces of cross-sectional image data generated by the cross-sectional image generation means 27, side by side. Alternatively, the display control means 31 may display a piece of cross-sectional image data which is generated by the cross-sectional image generation means 27 and has not been subjected to the spatial frequency processing (FIG. 5) and a piece of spatial frequency-processed cross-sectional image data (FIG. 9) side by side. In place of displaying the pieces of image data side by side, a piece of cross-sectional image data which has not been subjected to the spatial frequency processing and a piece of spatial frequency-processed cross-sectional image data may be displayed in different colors with being superimposed one on the other.

In this embodiment, the image data obtained by reconstructing the photoacoustic signals is subjected to the Fourier transform. Then, from the resulting spatial frequency domain image data, the given spatial frequency components are extracted and are subjected to the inverse Fourier transform. By using the spatial frequency filter as shown in FIG. 7, for example, unnecessary low-frequency components can be removed and high-frequency components (image noise) originating from tissues can be removed.

It should be noted that the photoacoustic signals, which are emitted from light-absorbing substances present in the subject, are detected by the individual detector elements with a time lag depending on the distance between the position of each light-absorbing substance and each detector element, and thus are not detected simultaneously by the detector elements. With the technique of Patent Document 1, the detection signals are subjected to the Fourier transform in the spatial direction. While this technique can achieve reduction of given low-frequency components from the spatial frequency domain detection signals, it cannot achieve extraction of blood vessels having a certain thickness. In contrast, in the present invention, the reconstructed image data is subjected to the Fourier transform. In this embodiment, the filtering is performed in a wave number space after the detection signals are converted into actual dimensions. This allows selecting a filter according to the blood vessel diameter information to set an appropriate filter to be used depending on the object to be observed, thereby allowing imaging of blood vessels having a desired thickness.

Figure 11:
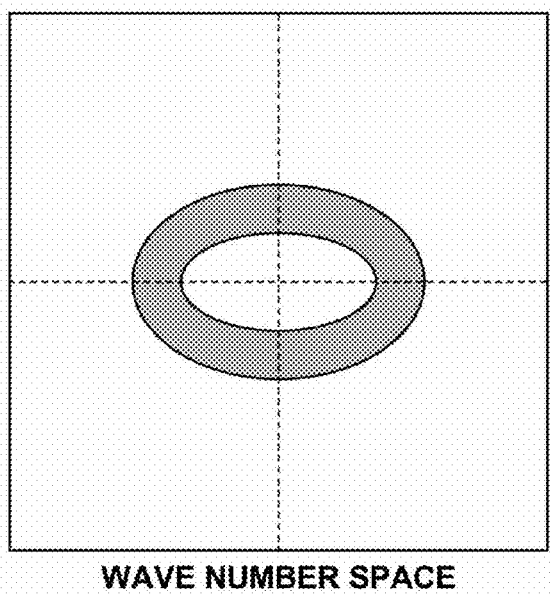
FIG. 11 is a diagram illustrating an elliptical spatial frequency filter.

It should be noted that, although the filter that transmits frequency components within a certain range of distance from the origin is used in the example shown in FIG. 7, the spatial frequency components to be extracted are not limited to those of the above-described example. A spatial frequency that is the lower limit of the transmission band and a spatial frequency that is the upper limit of the transmission band may be changed depending on the position in the wave number space. FIG. 11 shows an elliptical spatial frequency filter. If there is a high-intensity area in the wave number space, an elliptical spatial frequency filter with the high-intensity area being in the major-axis direction may be used. In a case where the spatial frequency filter shown in FIG. 11 is used, frequency components of higher frequencies are extracted in the kx-direction than in the ky-direction.

Figure 12:
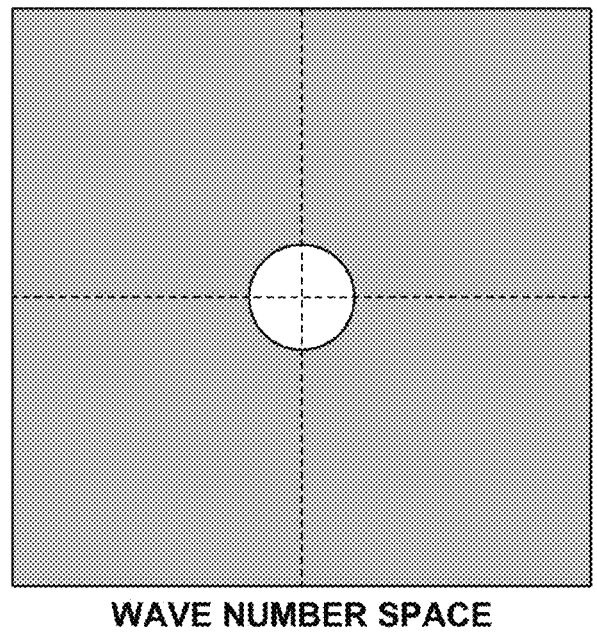
FIG. 12 is a diagram illustrating a spatial frequency filter for removing a low-frequency range.

Further, the spatial frequency filter is not limited to those that transmit spatial frequency components within a predetermined band. FIG. 12 shows a spatial frequency filter that removes a low frequency band. In a case where the spatial frequency filter shown in FIG. 12 is used, spatial frequency components of spatial frequencies higher than a certain spatial frequency can be extracted. The filter property of the spatial frequency filter is not limited to circular or elliptical and may be polygonal.

In this embodiment, a plurality of different wavelengths of light may be applied from the laser unit 13 to the subject, and photoacoustic waves emitted from the interior of the subject may be detected with the probe 11 after each of the plurality of wavelengths of light is applied. In this case, the photoacoustic image generation means generates a photoacoustic image by reconstructing photoacoustic signals detected for each of the plurality of wavelengths of light. The Fourier transform means 28 applies a Fourier transform to the photoacoustic image corresponding to each of the plurality of wavelengths of light. The spatial frequency processing means 29 extracts given spatial frequency components corresponding to each of the plurality of wavelengths of light from the Fourier-transformed spatial frequency domain image data corresponding to each wavelength, and the inverse Fourier transform means 30 applies an inverse Fourier transform to the extracted spatial frequency components corresponding to each wavelength.

For example, light of the first wavelength and light of the second wavelength may be emitted from the laser unit 13 and applied to the subject, and a photoacoustic image may be generated based on photoacoustic signals that are detected when the light of each wavelength is applied. For example, the first wavelength may correspond to imaging of blood (blood vessels), and the second wavelength may correspond to imaging of a chemical agent (contrast agent). Alternatively, the first wavelength may correspond to imaging of arteries, and the second wavelength may correspond to imaging of veins.

In the case where different objects are imaged with the first wavelength and the second wavelength, as described above, the spatial frequency processing means 29 can use spatial frequency filters having different frequency characteristics for the photoacoustic image data corresponding to the first wavelength and the photoacoustic image data corresponding to the second wavelength. In other words, the spatial frequency processing means 29 may extract different spatial frequency components from the spatial frequency domain photoacoustic image data corresponding to the light of the first wavelength and the spatial frequency domain photoacoustic image data corresponding to the light of the second wavelength. For example, if the difference of thickness of blood vessels between arteries and veins is known in advance, different spatial frequency components are extracted from the photoacoustic image corresponding to the first wavelength and the photoacoustic image corresponding to the second wavelength. By extracting spatial frequency components appropriate for the object imaged with the light of each wavelength, the desired object to be observed can be extracted from the photoacoustic image corresponding to each wavelength.

Figure 13:
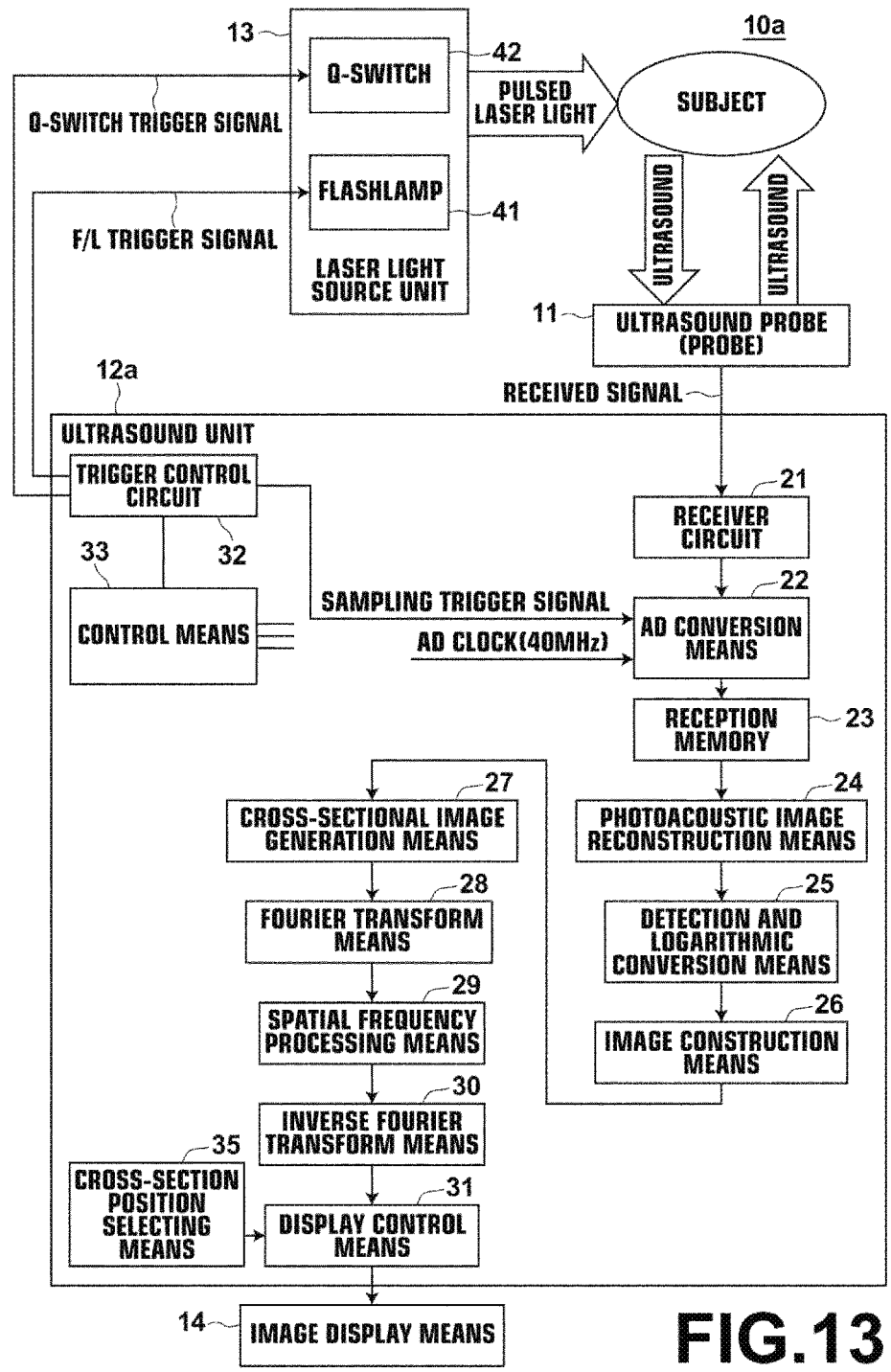
FIG. 13 is a block diagram illustrating a photoacoustic image generation device according to a second embodiment of the invention.

Next, a second embodiment of the invention is described. FIG. 13 shows a photoacoustic image generation device according to the second embodiment of the invention. A photoacoustic image generation device 10a of this embodiment differs from the photoacoustic image generation device 10 of the first embodiment shown in FIG. 1 in that the photoacoustic image generation device 10a further includes a cross-section position selecting means 35 in an ultrasound unit 12a. Other features may be the same as those of the first embodiment.

The cross-section position selecting means 35 determines a cross-section position of cross-sectional image data to be displayed on the display screen of the image display means 14 according to a user's operation. The display control means 31 displays, on the image display means 14, spatial frequency-processed cross-sectional image data corresponding to a cross-section position specified by the user. For example, the cross-section position selecting means 35 prompts the user to select the position of cross-sectional image data to be displayed among the pieces of cross-sectional image data shown in FIG. 4.

Figure 14:
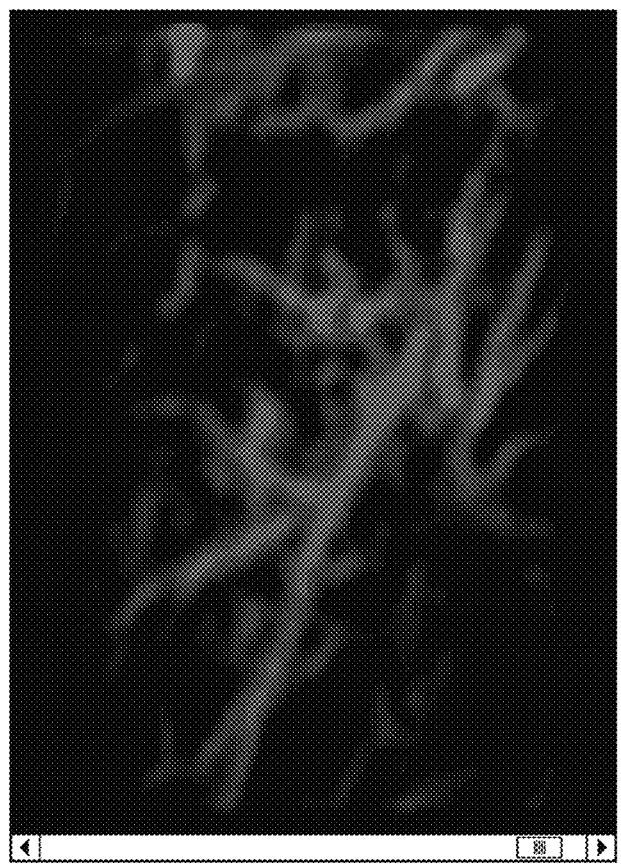
FIG. 14 shows an example of a display screen.

FIG. 14 shows an example of the display screen. For example, the display control means 31 displays a slide bar used to specify the cross-section position on the image display means 14. The cross-section position selecting means determines the position of a cross-section to be displayed according to operation of the slide bar by the user. For example, the left side of the slide bar in the drawing corresponds to shallower positions of the subject and the right side corresponds to deeper positions. When the user operates the slide bar, the cross-section position of the spatial frequency-processed cross-sectional image data displayed above the slide bar is changed according to the operation. The slide bar may not necessarily be located below the cross-sectional image data, and may be located above, on the left, or on the right of the cross-sectional image data. Also, the slide bar may not necessarily be attached to the cross-sectional image data as long as it is displayed somewhere on the display screen.

In this embodiment, the cross-section position selecting means 35 selects the cross-section position of cross-sectional image data to be displayed according to a user's operation, and the display control means 31 displays the spatial frequency-processed cross-sectional image data at the selected cross-section position. The user can display a cross-sectional image at any cross-section position by operating the cross-section position selecting means 35. Further, by operating the slide bar, or the like, so as to continuously change the cross-section position, for example, the user can observe the photoacoustic image in a manner like a moving image. Other effects are the same as those of the first embodiment.

Figure 15:
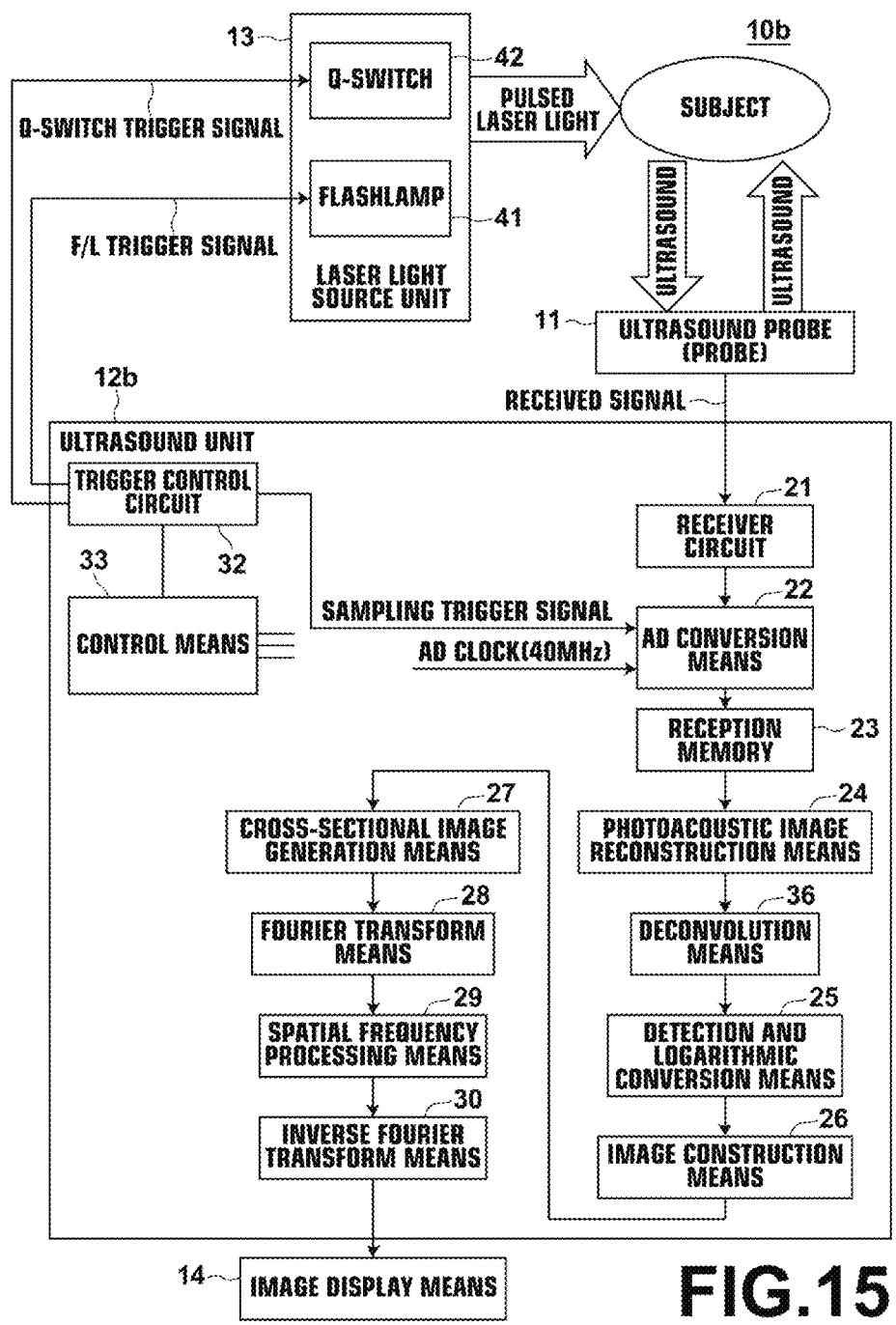
FIG. 15 is a block diagram illustrating a photoacoustic image generation device according to a third embodiment of the invention.

Next, a third embodiment of the invention is described. FIG. 15 shows a photoacoustic image generation device according to the third embodiment of the invention. A photoacoustic image generation device 10b of this embodiment differs from the photoacoustic image generation device 10 of the first embodiment shown in FIG. 1 in that the photoacoustic image generation device 10b further includes a deconvolution means 36 in an ultrasound unit 12b. Other features may be the same as those of the first embodiment.

The deconvolution means 36 generates, from the photoacoustic signals reconstructed by the photoacoustic image reconstruction means 24, signals from which a light differential waveform, which is a differential waveform of a temporal waveform of light intensity of the light applied to the subject, is deconvolved. The deconvolution means 36 converts the reconstructed photoacoustic signals from the time domain signals to frequency domain signals by using, for example, a discrete Fourier transform. The deconvolution means 36 also converts the light differential waveform from the time domain signal to a frequency domain signal by using a discrete Fourier transform. The deconvolution means 36 calculates an inverse of the Fourier transformed light differential waveform as an inverse filter, and applies the inverse filter to the Fourier-transformed frequency domain photoacoustic signals. By applying the inverse filter, the light pulse differential waveform is deconvolved from the frequency domain signals. Thereafter, the photoacoustic signals processed with the inverse filter are converted from the frequency domain signals to time domain signals by an inverse Fourier transform. In place of deconvolving the light differential waveform from the reconstructed photoacoustic signals, the light differential waveform may be deconvolved from the photoacoustic signals before the reconstruction.

Now, the deconvolution of the light differential waveform is described. It is assumed here that micro absorptive particles, which are light-absorbing substances, absorb pulsed laser light and pressure waves (photoacoustic pressure waves) are emitted. According to [LG. Calasso et al., "Photoacoustic Point Source", PHYSICAL REVIEW LETTERS, Vol. 86, No. 16, pp. 3550-3553, 2001], a pressure waveform $p_{micro}(R,t)$, which is a photoacoustic pressure wave emitted from a micro absorptive particle at a position r and observed at a position R at a clock time t, is a spherical wave of the equation below:

$$p_{micro}(R,t) = \frac{k}{|r-R|} \frac{d}{d\left(t - \frac{|r-R|}{v_s}\right)} I\left(t - \frac{|r-R|}{v_s}\right)$$

where I(t) is a temporal waveform of light intensity of the excitation light, the coefficient k is a conversion factor when the particle absorbs light and emits the acoustic wave, and $v_s$ is a speed of sound in the subject. Each of the positions r and R is a vector representing a spatial position. As shown by the equation above, the pressure emitted from the micro absorptive particle is a spherical wave that is proportional to the light pulse differential waveform.

A pressure waveform obtained from an actual object to be imaged has a size of a more macro absorptive substance, and therefore is assumed to be a waveform formed by superposing above-described pressure waveforms of the micro absorptive particles (the superposition principle). It is assumed here that an absorption distribution of particles that emit a macro photoacoustic wave is A(r−R), and an observed waveform of the pressure from the macro absorptive substance is $p_{macro}(R,t)$. At the observation position R, a photoacoustic wave from an absorptive particle located at a radius $v_s t$ from the observation position R is observed at each clock time. Therefore, the observed waveform $p_{macro}(R,t)$ is expressed as the pressure waveform equation below:

$$p_{macro}(R, t) = \quad (1)$$

$$\iiint A(r-R) \times \frac{k}{|r-R|} \frac{d}{d\left(t - \frac{|r-R|}{v_s}\right)} I\left(t - \frac{|r-R|}{v_s}\right) dV =$$

$$\int_0^\pi \int_{-\frac{\pi}{2}}^{\frac{\pi}{2}} \int_0^{|r-R|=v_s t} \frac{k A(r-R)}{|r-R|}$$

$$I'\left(t - \frac{|r-R|}{v_s}\right) |r-R|^2 \sin\theta \, d|r-R| \, d\theta \, d\phi =$$

$$\int_0^{|r-R|=v_s t} \frac{k}{|r-R|} \int_0^\pi \int_{-\frac{\pi}{2}}^{\frac{\pi}{2}} A(r-R) dS \times I'\left(t - \frac{|r-R|}{v_s}\right) d|r-R| = \Bigg[$$

$$\frac{k}{|r-R|} \int_0^\pi \int_{-\frac{\pi}{2}}^{\frac{\pi}{2}} A(r-R) dS \Bigg] * \left[I'\left(t - \frac{|r-R|}{v_s}\right)\right]$$

As can be seen from the equation (1) above, the observed waveform shows a convolution type of light pulse differential. By deconvolving the light pulse differential waveform from the observed waveform, an absorptive substance distribution is obtained.

In this embodiment, the differential waveform of the light applied to the subject is deconvolved from the detected photoacoustic signals. By deconvolving the light differential waveform, a distribution of light-absorbing substances can be obtained, and this allows generating an absorption distribution image. Imaging a distribution of absorptive substances facilitates checking positions of blood vessels, etc., in the spatial frequency-processed cross-sectional image. Other effects are the same as those of the first embodiment.

It should be noted that the manner of presenting the spatial frequency-processed photoacoustic image data to the user is not limited to one shown in FIG. 9, where a cross-sectional image is displayed, and the spatial frequency-processed photoacoustic image data may be presented in any manner. For example, processing to extract predetermined frequency zone components may be applied to three-dimensional photoacoustic image data. Then, based on the resulting spatial frequency-processed three-dimensional photoacoustic image data, a projection image may be generated by using a maximum value projection method, or the like, to display the projection image on the image display means 14. Alternatively, three-dimensional display may be performed by performing volume rendering, or the like, on the three-dimensional photoacoustic image data.

Although the examples where the cross-sectional image generation means 27 is used and the Fourier transform means 28 applies a two-dimensional Fourier transform to the cross-sectional images are described in the above-described embodiments, this is not intended to limit the invention. Without using the cross-sectional image generation means 27, the Fourier transform means 28 may apply a three-dimensional Fourier transform to three-dimensional photoacoustic image data. Also in this case, blood vessels, or the like, having a desired thickness can be imaged by extracting a predetermined spatial frequency band.

Although the Fourier transform means 28 applies a Fourier transform to the image generated by the image construction means 26 in the above-described embodiments, the signals to which the Fourier transform means 28 applies a Fourier transform only need to have been at least reconstructed by the photoacoustic signal reconstruction means 24, and are not limited to the signals of the image generated by the image construction means 26. The Fourier transform means 28 may apply a Fourier transform to signals outputted from the photoacoustic image reconstruction means 24. In this case, the detection and logarithmic conversion and the following operations may be performed on signals resulting from an inverse transform by the inverse Fourier transform means 30.

Although the examples where a blood vessel portion is mainly imaged are described in the above-described embodiments, this is not intended to limit the invention. For example, in a case were a photoacoustic image of a tubular structure, such as nerves or lymphatic vessels, is generated, the structure of a desired size can be imaged by extracting given frequency components in the spatial frequency domain.

The present invention has been described based on preferred embodiments thereof. However, the photoacoustic image generation device of the invention is not limited to those of the above-described embodiments, and various modifications and changes made to the above-described embodiments are also within the scope of the invention.

What is claimed is:

1. A photoacoustic image generation device comprising:
a light source that emits light to be applied to a subject;
an acoustic wave detection unit that detects photoacoustic waves emitted from the interior of the subject due to the light applied to the subject;
a photoacoustic image generation unit that reconstructs photoacoustic signals to generate image data, the photoacoustic signals being detection signals of the photoacoustic waves;
a Fourier transform unit that applies a Fourier transform in a two-dimensional or higher dimensional space to the image data to generate spatial frequency domain image data;
a spatial frequency processing unit that extracts given spatial frequency components from the spatial frequency domain image data; and
an inverse Fourier transform unit that applies an inverse Fourier transform to the extracted spatial frequency components to generate spatial frequency-processed image data
wherein the spatial frequency processing unit extracts spatial frequency components of frequencies not lower than a first spatial frequency and not higher than a second spatial frequency that is higher than the first spatial frequency.

2. The photoacoustic image generation device as claimed in claim 1, wherein the first spatial frequency and the second spatial frequency are changed depending on a position in the spatial frequency domain.

3. The photoacoustic image generation device as claimed in claim 1, wherein the spatial frequency processing unit determines the given spatial frequency components to be extracted according to an observation object condition specified by the user.

4. The photoacoustic image generation device as claimed in claim 1, further comprising a cross-sectional image generation unit that cuts out, from three-dimensional image data based on three-dimensionally detected photoacoustic waves, a cross-section along a plane perpendicular to one of axes forming a three-dimensional space, and generates cross-sectional image data by combining image data within a predetermined range in a direction along the one axis including the cut-out cross-section,
    wherein the Fourier transform unit applies a two-dimensional Fourier transform to the cross-sectional image data.

5. The photoacoustic image generation device as claimed in claim 4, wherein
    the cross-sectional image generation unit cuts out cross-sections at a plurality of positions along the one axis to generate pieces of cross-sectional image data,
    the Fourier transform unit applies a Fourier transform to each of the generated pieces of cross-sectional image data to generate pieces of spatial frequency domain image data,
    the spatial frequency processing unit extracts given spatial frequency components from each of the generated pieces of spatial frequency domain image data, and
    the inverse Fourier transform unit applies an inverse Fourier transform to the given spatial frequency components extracted from each of the pieces of spatial frequency domain image data to generate spatial frequency-processed cross-sectional image data for each of the pieces of cross-sectional image data.

6. The photoacoustic image generation device as claimed in claim 5, wherein the cross-sectional image generation unit cuts out the cross-sections at equal intervals.

7. The photoacoustic image generation device as claimed in claim 4, wherein the cross-sectional image generation unit cuts out the cross-section in a direction parallel to an acoustic wave detection surface of the acoustic wave detection unit while changing the position of the cut-out cross-section along an axis corresponding to a depth direction of the subject.

8. The photoacoustic image generation device as claimed in claim 4, wherein the cross-sectional image generation unit combines the image data within the predetermined range by projecting maximum values of the image data within the predetermined range or integrating the image data within the predetermined range.

9. The photoacoustic image generation device as claimed in claim 4, further comprising an image display control unit that displays, on a display device, spatial frequency-processed cross-sectional image data obtained by applying an inverse Fourier transform to given spatial frequency components extracted from the spatial frequency domain cross-sectional image data.

10. The photoacoustic image generation device as claimed in claim 9, further comprising a cross-section position selection unit that determines a cross-section position of cross-sectional image data to be displayed according to a user's operation, wherein the display control unit displays, on the display device, the spatial frequency-processed cross-sectional image data corresponding to a cross-section position specified by the user.

11. The photoacoustic image generation device as claimed in claim 10, wherein the display control unit displays, on the display device, a slide bar used to specify the cross-section position, and the cross-section position selection unit determines the cross-section position according to operation of the slide bar by the user.

12. The photoacoustic image generation device as claimed in claim 9, wherein the display control unit displays cross-sectional image data that has not been subjected to spatial frequency processing and the spatial frequency-processed cross-sectional image data side by side on the display device.

13. The photoacoustic image generation device as claimed in claim 9, wherein the display control unit binarizes the spatial frequency-processed cross-sectional image data and displays the binarized spatial frequency-processed cross-sectional image data on the display device.

14. The photoacoustic image generation device as claimed in claim 1, wherein the Fourier transform unit applies a three-dimensional Fourier transform to three-dimensional image data based on three-dimensionally detected photoacoustic waves.

15. The photoacoustic image generation device as claimed in claim 1, wherein
    the light source emits a plurality of different wavelengths of light,
    the acoustic wave detection unit detects photoacoustic waves emitted from the interior of the subject after each of the plurality of wavelengths of light is applied to the subject,
    the photoacoustic image generation unit reconstructs the detected photoacoustic signals corresponding to each of the plurality of wavelengths of light to generate image data,
    the Fourier transform unit applies a Fourier transform to the image data corresponding to each of the plurality of wavelengths of light,
    the spatial frequency processing unit extracts given spatial frequency components corresponding to each of the plurality of wavelengths of light from the Fourier-transformed spatial frequency domain image data corresponding to each wavelength, and
    the inverse Fourier transform unit applies an inverse Fourier transform to each of the extracted spatial frequency components.

16. The photoacoustic image generation device as claimed in claim 1, further comprising a deconvolution unit that deconvolves, from the photoacoustic signals, a differential waveform of the light applied to the subject.

17. A photoacoustic image generation method comprising the steps of:
    applying light to a subject, and then detecting photoacoustic waves emitted from the interior of the subject due to the light applied to the subject;
    reconstructing photoacoustic signals to generate image data, the photoacoustic signals being detection signals of the photoacoustic waves;
    applying a Fourier transform in a two-dimensional or higher dimensional space to the image data to generate spatial frequency domain image data;
    extracting given spatial frequency components from the spatial frequency domain image data, wherein the given spatial frequency components have frequencies not lower than a first spatial frequency and not higher than a second spatial frequency that is higher than the first spatial frequency; and
    applying an inverse Fourier transform to the extracted spatial frequency components to generate spatial frequency-processed image data.

18. A photoacoustic image generation device comprising:
    a light source that emits light to be applied to a subject;
    an acoustic wave detection unit that detects photoacoustic waves emitted from the interior of the subject due to the light applied to the subject;

a photoacoustic image generation unit that reconstructs photoacoustic signals to generate image data, the photoacoustic signals being detection signals of the photoacoustic waves;

a Fourier transform unit that applies a Fourier transform in a two-dimensional or higher dimensional space to the image data to generate spatial frequency domain image data;

a spatial frequency processing unit that extracts given spatial frequency components from the spatial frequency domain image data; and an inverse Fourier transform unit that applies an inverse Fourier transform to the extracted spatial frequency components to generate spatial frequency-processed image data, wherein the light source emits a plurality of different wavelengths of light, the acoustic wave detection unit detects photoacoustic waves emitted from the interior of the subject after each of the plurality of wavelengths of light is applied to the subject, the photoacoustic image generation unit reconstructs the detected photoacoustic signals corresponding to each of the plurality of wavelengths of light to generate image data, the Fourier transform unit applies a Fourier transform to the image data corresponding to each of the plurality of wavelengths of light, the spatial frequency processing unit extracts given spatial frequency components corresponding to each of the plurality of wavelengths of light from the Fourier-transformed spatial frequency domain image data corresponding to each wavelength, and the inverse Fourier transform unit applies an inverse Fourier transform to each of the extracted spatial frequency components.

19. The photoacoustic image generation device as claimed in claim 18, wherein the plurality of wavelengths of light comprise light of a first wavelength and light of a second wavelength, and the spatial frequency components extracted by the spatial frequency processing unit from the spatial frequency domain image data corresponding to the light of the first wavelength and the spatial frequency components extracted by the spatial frequency processing unit from the spatial frequency domain image data corresponding to the light of the second wavelength are different from each other.

20. The photoacoustic image generation device as claimed in claim 1, wherein the spatial frequency processing unit extracts frequency components within a certain range of distance from a predetermined position, from the spatial frequency domain image data, such that the extracted transmits frequency components corresponds to size of a target structure.

* * * * *